US008529884B2

(12) United States Patent
Weiner et al.

(10) Patent No.: US 8,529,884 B2
(45) Date of Patent: Sep. 10, 2013

(54) COSMID DNA CONSTRUCTS AND METHODS OF MAKING AND USING SAME

(75) Inventors: David B. Weiner, Merion Station, PA (US); Jeong-Im Sin, Daegu (KR); Donghui Zhang, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 2375 days.

(21) Appl. No.: 10/168,694

(22) PCT Filed: Dec. 22, 2000

(86) PCT No.: PCT/US00/35033
§ 371 (c)(1),
(2), (4) Date: Dec. 9, 2002

(87) PCT Pub. No.: WO01/45749
PCT Pub. Date: Jun. 28, 2001

(65) Prior Publication Data

US 2008/0219953 A1 Sep. 11, 2008

Related U.S. Application Data

(60) Provisional application No. 60/171,541, filed on Dec. 22, 1999.

(51) Int. Cl.
*A01N 63/00* (2006.01)
*A01N 43/04* (2006.01)

(52) U.S. Cl.
USPC .......... 424/93.2; 514/44

(58) Field of Classification Search
USPC .......... 424/93.2; 514/44
See application file for complete search history.

(56) References Cited

U.S. PATENT DOCUMENTS

| | | | | | |
|---|---|---|---|---|---|
| 4,746,539 | A | * | 5/1988 | Webb et al. | 435/7.93 |
| 4,945,050 | A | | 7/1990 | Sanford et al. | |
| 5,036,006 | A | | 7/1991 | Sanford et al. | |
| 5,580,859 | A | | 12/1996 | Felgner et al. | |
| 5,589,466 | A | | 12/1996 | Felgner et al. | |
| 5,593,972 | A | | 1/1997 | Weiner et al. | |
| 5,703,057 | A | | 12/1997 | Johnston et al. | |
| 5,739,118 | A | | 4/1998 | Carrano et al. | |
| 5,817,637 | A | | 10/1998 | Weiner et al. | |
| 5,830,876 | A | | 11/1998 | Weiner et al. | |
| 5,837,533 | A | | 11/1998 | Boutin | |
| 5,962,428 | A | | 10/1999 | Carrano et al. | |
| 5,981,505 | A | | 11/1999 | Weiner et al. | |
| 6,110,898 | A | * | 8/2000 | Malone et al. | 514/44 |
| 6,468,982 | B1 | * | 10/2002 | Weiner et al. | 514/44 |
| 6,573,090 | B1 | * | 6/2003 | Breakefield et al. | 435/320.1 |
| 6,605,284 | B2 | * | 8/2003 | Ueda et al. | 424/212.1 |

FOREIGN PATENT DOCUMENTS

| | | | |
|---|---|---|---|
| WO | WO90/11092 | | 10/1990 |
| WO | WO93/23552 | | 11/1993 |
| WO | WO94/16737 | | 8/1994 |
| WO | WO 96/21007 | | 7/1996 |
| WO | WO 96/40965 | | 12/1996 |
| WO | WO 97/40183 | | 10/1997 |
| WO | WO97/44446 | | 11/1997 |
| WO | WO 97/44446 | A1 * | 11/1997 |
| WO | WO 01/32221 | | 5/2001 |

OTHER PUBLICATIONS

Tao and Zhang, 1998, Nucleic Acids Research, 26: 4901-4909.*
Craig et al., 1990, Nucleic Acids Research 18: 2653-2660.*
Stratagene, SuperCos 1 Cosmid Vector Kit, Instruction Manual [online], 2005 [retrieved on Jul. 20, 2007]. Retrieved from the Internet: < URL: http://www.cultek.com/inf/otros/soluciones/DNA-recombinante/251301.pdf >, pp. 1-23.*
Manickan et al., 1995, Journal of Immunology, 155: 259-265.*
Stanberry, 2004, Herpes, 11, Supplement 3: 161A-169A.*
Whitley et al., 2002, J. Clin. Invest., 109: 145-151.*
Barry et al., 1997, Vaccine, 15: 788-791.*
Cunningham et al., "A cosmid-based system for constructing mutants of herpes simplex virus type 1", *Virology*, 1993; 197(1):116-24.
Birren, et al., EMBL Acc. No. AC011116, Oct. 6, 1999.
Deneris, et al., "Beta3: A New Member of Nicotinic Acetylcholine Receptor gene Family Is Expressed in Brain," J. Biol. Chem. (1989) 264(11):6266-6272.
Adams, et al., EMBL Acc. No. AQ315444, Dec. 23, 1998.
Wolff et al, "Direct gene Transfer into Mouse In Vivo," Science (1990) 247-1465-1468.
Nabel, et al., "Site-Specific Gene Expression in vivo by Direct Gene Transfer into the Arterial Wall," Science (1990) 249:1285-1288.
Ascadi, et al., "Human Dystrophin Expression in Mdx Mice After Intramuscular Injection of DNA Constructs," Nature (1991)352:815-818.
Felgner et al, "Gene Therapeutics," Nature (1991) 351-352.
Wolff, et al., "Conditions Affecting Direct Gene Transfer into Rodent Muscle in Vivo," BioTechniques (1991) 11:474-485.

* cited by examiner

*Primary Examiner* — Michael C. Wilson
(74) *Attorney, Agent, or Firm* — Pepper Hamilton, LLP

(57) ABSTRACT

Methods of inducing immune responses in individuals against a pathogen are disclosed. Methods of treating individuals susceptible to or suffering from a disease associated with a genetic defect which results in the non-production or under production of a protein or the production of a non-functioning or partially functioning protein are disclosed. Methods of delivering a protein to an individual are disclosed. Pharmaceutical compositions that comprise cosmids are disclosed.

4 Claims, 3 Drawing Sheets

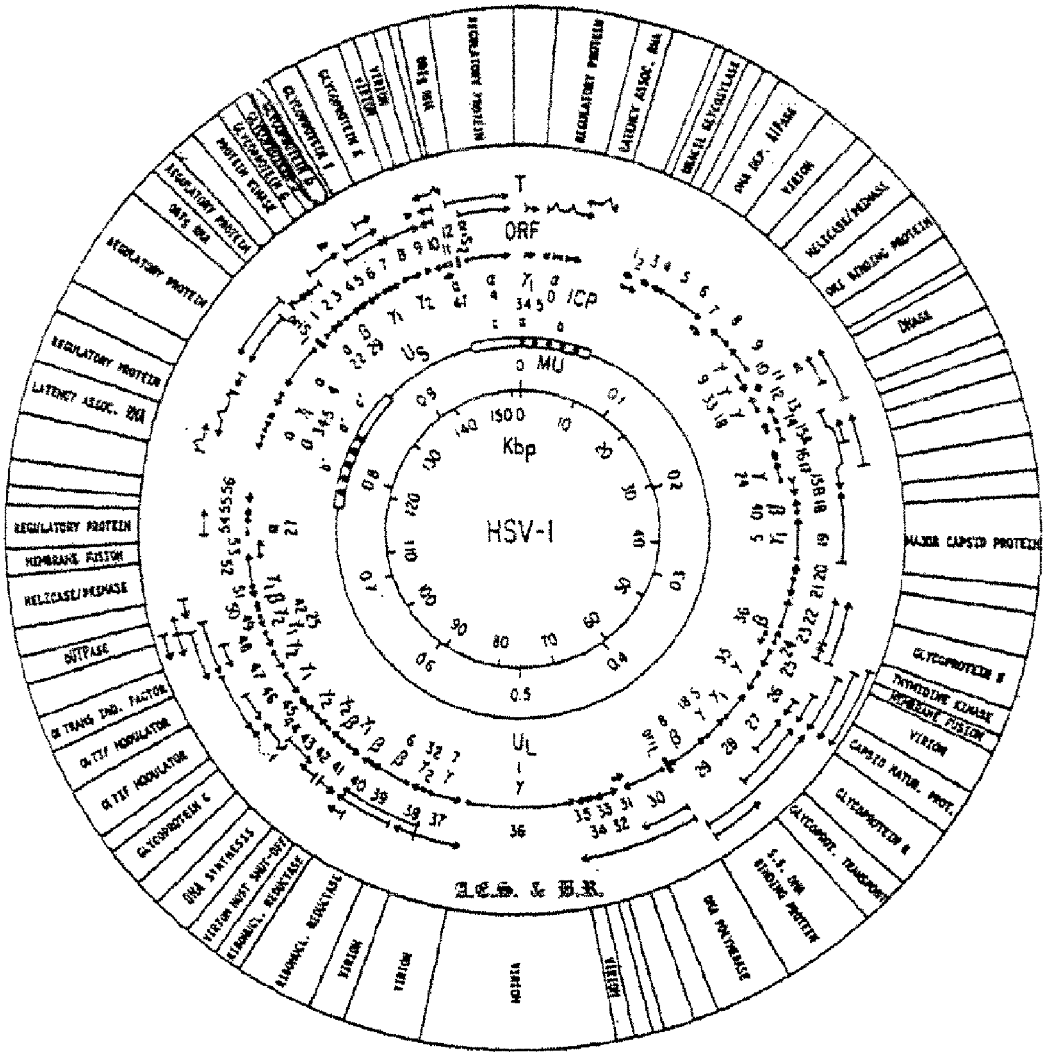

Functional organization of the HSV-1 genome. The circles are described from inside out. *Circle 1*: Map units and kilobase pairs. *Circle 2*: Sequence arrangement of HSV genome shown as a *circularized version of* the P arrangement. Cleavage of the circle at O map units would yield a linear molecule in the P arrangement. The letters *a*, *b*, *c*, $U_L$, and $U_S$ identify different domains of the genome. *Circle 3*: Representation of the open-reading frames. The letters and numbers indicate the regulatory class ($\alpha$, $\beta$, $\gamma_1$, or $\gamma_2$) to which the gene belongs, and they also indicate the ICP designation of the product. The numbers outside the circle indicate the open-reading frames according to McGeoch et al. (294,298). *Circle 4*: This represents the direction and approximate size of the transcripts as described by numerous laboratories. *Circle 5*: This lists the known functions of the proteins specified by the open-reading frames. Note that virion structural proteins are listed either as "glycoprotein" or "virion." The genes dispensable for growth in cells in culture are listed in the text. The data for circles 3 and 4 are derived from refs. 6, 39, 57, 71, 72, 74, 82, 86, 89, 101, 113, 139, 146, 162, 178, 296–300, 304, 305, 310, 311, 330, 353, 354, 358, 393, 398, 400, 401, 459, 524, and 532. The references for gene functions (circle 5) are listed in the text.

FIGURE 1

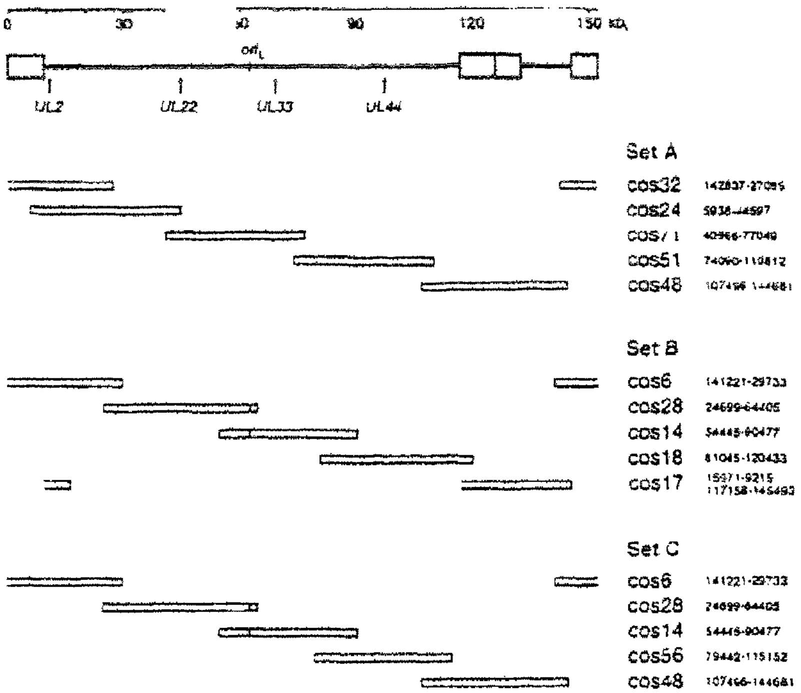

*Locations of cosmid inserts with respect to the HSV-1 genome.* The genome is depicted as two unique regions (horizontal lines), the larger $U_L$ and the smaller $U_S$, flanked by inverted repeats (rectangles). The four *XbaI* sites are indicated by vertical arrows, and the genes within whose protein-coding regions they are located are indicated. Locations of cosmid inserts are indicated by open bars, and their precise locations in the sequence are given in base pairs on the right. The position of $ori_L$ is denoted by vertical lines in appropriate $ori_L^+$ *cosmids*.

FIGURE 2

COSMID DNA CONSTRUCTS AND METHODS OF MAKING AND USING SAME

CROSS-REFERENCE TO RELATED APPLICATIONS

This application claims priority to, and is a U.S. National Stage filing under 35 USC §371 of, International PCT Application Serial No. PCT/US00/35033, filed Dec. 22, 2000, which claims priority to U.S. Provisional Application No. 60/171,541, filed Dec. 22, 1999.

FIELD OF THE INVENTION

The present invention relates to compositions and methods for introducing genetic material into the cells of an individual. The compositions and methods of the invention can be used to deliver protective and/or therapeutic agents including genetic material that encodes protein targets for prophylactic and or therapeutic immunization and non-immunogenic therapeutic proteins. The present invention relates to DNA cosmids which comprise expressible forms of nucleotide sequences that encode immunogenic proteins or non-immunogenic therapeutic proteins, to pharmaceutical compositions comprising the same, to methods of inducing immune responses in individuals against immunogens, and to methods for prophylactically and/or therapeutically treating individuals by providing therapeutic proteins.

BACKGROUND OF THE INVENTION

Vaccines are useful to immunize individuals against target immunogens such as pathogen antigens, allergens or antigens associated with cells involved in human diseases. Antigens associated with cells involved in human diseases include cancer-associated tumor antigens and antigens associated with cells involved in autoimmune diseases.

In designing such vaccines, it has been recognized that vaccines which produce the target antigen in the cell of the vaccinated individual are effective in inducing the cellular arm of the immune system. Specifically, live attenuated vaccines, recombinant vaccines which use a virulent vectors and DNA vaccines all lead to the production of antigens in the cell of the vaccinated individual which results induction of the cellular arm of the immune system. On the other hand, killed or inactivated vaccines and sub-unit vaccines which comprise only proteins do induce a humoral response but do not induce good cellular immune responses.

A cellular immune response is often necessary to provide protection against pathogen infection and to provide effective immune-mediated therapy for treatment of pathogen infection, cancer or autoimmune diseases. Accordingly, vaccines which produce the target antigen in the cell of the vaccinated individual such as live attenuated vaccines, recombinant vaccines which use a virulent vectors and DNA vaccines are preferred.

While such vaccines are often effective to immunize individuals prophylactically or therapeutically against pathogen infection or human diseases, there is a need for improved vaccines. There is a need for compositions and methods which produce an enhanced immune response.

Apart from prophylactic and therapeutic immunity, immune responses can be induced as a means to obtain compositions such as antibody compositions which include antibodies directed at a particular immunogen.

Gene therapy, in contrast to immunization, uses nucleic acid molecules that encode non-immunogenic proteins whose expression confers a therapeutic benefit to an individual to whom the nucleic acid molecules are administered. A specific type of gene therapy relates to the delivery of genetic material which encodes non-immunogenic proteins that modulate immune responses in the individual and thus confer a therapeutic benefit. For example, protocols can be designed to deliver genetic material which encodes non-immunogenic proteins that downregulate immune responses associated with an autoimmune disease in an individual and thus confer a therapeutic benefit to the individual. There is a need for compositions and methods which can be used in gene therapy protocols to modulate immune responses.

Modulation of immune responses by alternative means is similarly desirable to treat diseases such as autoimmune disease and cell/tissue/organ rejection. There is a need for compositions and methods which can be used to modulate immune responses and to design and discover compositions useful to modulate immune responses.

The direct introduction of a normal, functional gene into a living animal has been studied as a means for replacing defective genetic information. In some studies, DNA is introduced directly into cells of a living animal without the use of a viral particle or other infectious vector. Nabel, E. G., et al., (1990) *Science* 249:1285-1288, disclose site-specific gene expression in vivo of a beta-galactosidase gene that was transferred directly into the arterial wall in mice. Wolfe, J. A. et al., (1990) *Science* 247:1465-1468, disclose expression of various reporter genes that were directly transferred into mouse muscle in vivo. Acsadi G., et al., (1991) *Nature* 352:815-818, disclose expression of human dystrophin gene in mice after intramuscular injection of DNA constructs. Wolfe, J. A., et al., 1991 *BioTechniques* 11(4):474-485, which is incorporated herein by reference, refers to conditions affecting direct gene transfer into rodent muscle in vivo. Feigner, P. L. and G. Rhodes, (1991) *Nature* 349:351-352, disclose direct delivery of purified genes in vivo as drugs without the use of retroviruses.

The direct injection of DNA in both protective and therapeutic immunization protocols as well as non-immunogenic therapies is described in U.S. Pat. No. 5,593,972, U.S. Pat. No. 5,589,466, U.S. Pat. No. 5,830,876, U.S. Pat. No. 5,817,637, U.S. Pat. No. 5,981,505, U.S. Pat. No. 5,739,118, U.S. Pat. No. 5,962,428, U.S. Pat. No. 5,837,533, PCT/US90/01515, PCT/US93/02338, PCT/US93/048131, and PCT/US94/00899, which are each incorporated herein by reference. In addition to the delivery protocols described in those applications, alternative methods of delivering DNA are described in U.S. Pat. Nos. 4,945,050 and 5,036,006, which are both incorporated herein by reference. Essentially, gene constructs are delivered directly to individuals free of infectious agents such as replicating or non-replicating viral particles.

There remains a need for more effective compositions and methods of inducing immune responses and delivering therapeutic proteins.

SUMMARY OF THE INVENTION

The present invention relates to methods of inducing immune responses in individuals against a pathogen. The methods comprise the step of administering to the individual a cosmid that comprises at least 50 kilobases of DNA including coding nucleotide sequences that encode one or more proteins including at least one immunogenic protein. The coding nucleotide sequences are operably linked to regulatory elements that are functional in cells of the individual. The cosmid is taken up by cells in the individual, the coding nucleotide sequences are expressed and an immune response against the immunogenic pathogen protein is induced in the individual. The immune response against the immunogenic protein is cross reactive to a pathogen antigen. The immunogenic protein may be an immunogenic pathogen protein. The cosmid may comprises 80-100 or more kilobases of DNA.

The present invention relates to methods of treating individuals susceptible to or suffering from a diseases associated with a genetic defect which results in the non-production or underproduction of a protein or the production of a non-functioning or partially functioning protein. The methods comprise the step of providing to the individual a cosmid that includes DNA that encodes a compensating protein to compensate for the non-produced, underproduced, non-functioning or partially functioning protein. The cosmid comprises at least 50 kilobases of DNA including a coding nucleotide sequence that encode the compensating protein operably linked to regulatory elements that are functional in cells of said individual, wherein said cosmid is taken up by cells in said individual, said coding nucleotide sequence is expressed and the compensating protein is produced in an amount effective to compensate for the non-produced, underproduced, non-functioning or partially functioning protein. The cosmid may comprises 80-100 or more kilobases of DNA.

The present invention relates to a method of delivering a protein to an individual comprising the step of administering to the individual a cosmid that comprises at least 50 kilobases of DNA including a coding nucleotide sequence that encode the protein. The coding nucleotide sequence is operably linked to regulatory elements that are functional in cells of the individual. The cosmid is taken up by cells in the individual, the coding nucleotide sequence is expressed and the protein is produced. The cosmid may comprises 80-100 or more kilobases of DNA.

The present invention relates to pharmaceutical compositions that comprise a cosmid which comprises at least 50 kilobases of DNA including coding nucleotide sequences that encode one or more proteins including at least one immunogenic protein which is immunogenically cross reactive with a pathogen antigen. The coding nucleotide sequences are operably linked to regulatory elements. The pharmaceutical composition may further comprise a DNA vaccine facilitator.

The present invention relates to pharmaceutical compositions that comprise a cosmid which comprises at least 50 kilobases of DNA including coding nucleotide sequences that encode one or more proteins including at least one non-immunogenic protein. The coding nucleotide sequences are operably linked to regulatory elements. The pharmaceutical composition may further comprise a DNA vaccine facilitator.

BRIEF DESCRIPTION OF THE DRAWINGS

FIG. 1 shows the functional organization of the HSV-1 genome. The circles are described from inside out. Circle 1: Map units and kilobase pairs. Circle 2: Sequence arrangement of HSV genome shown as a circularized version of the P arrangement. Cleavage of the circle at O map units would yield a linear molecule in the P arrangement. The letters a, b, c, $U_L$ and $U_S$ identify different domains of the genome. Circle 3: Representation of the open-reading frames. The letters and numbers indicate the regulatory class (α, β, $\gamma_1$ or $\gamma_2$) to which the gene belongs, and they also indicate the ICP designation of the product. The numbers outside the circle indicate the open-reading frames according to McGeoch et al. (294,298). Circle 4: This represents the direction and approximate size of the transcripts as described by numerous laboratories. Circle 5: This lists the known functions of the proteins specified by the open-reading frames. Note that virion structural proteins are listed either as "glycoprotein" or "virion." The genes dispensable for growth in cells in culture are listed in the text. The data for circles 3 and 4 are derived from refs. 6, 39, 57, 71, 72, 74, 82, 86, 89, 101, 113, 139, 146, 162, 178, 296-300, 304, 305, 310, 311, 330, 353, 354, 358, 393, 398, 400, 401, 459, 524, and 532. The references for gene functions circle 5 are listed in the text.

FIG. 2 shows various recombinant cosmids constructed using incomplete HSV-1 genome inserts.

DETAILED DESCRIPTION OF PREFERRED EMBODIMENTS

Figure 3:
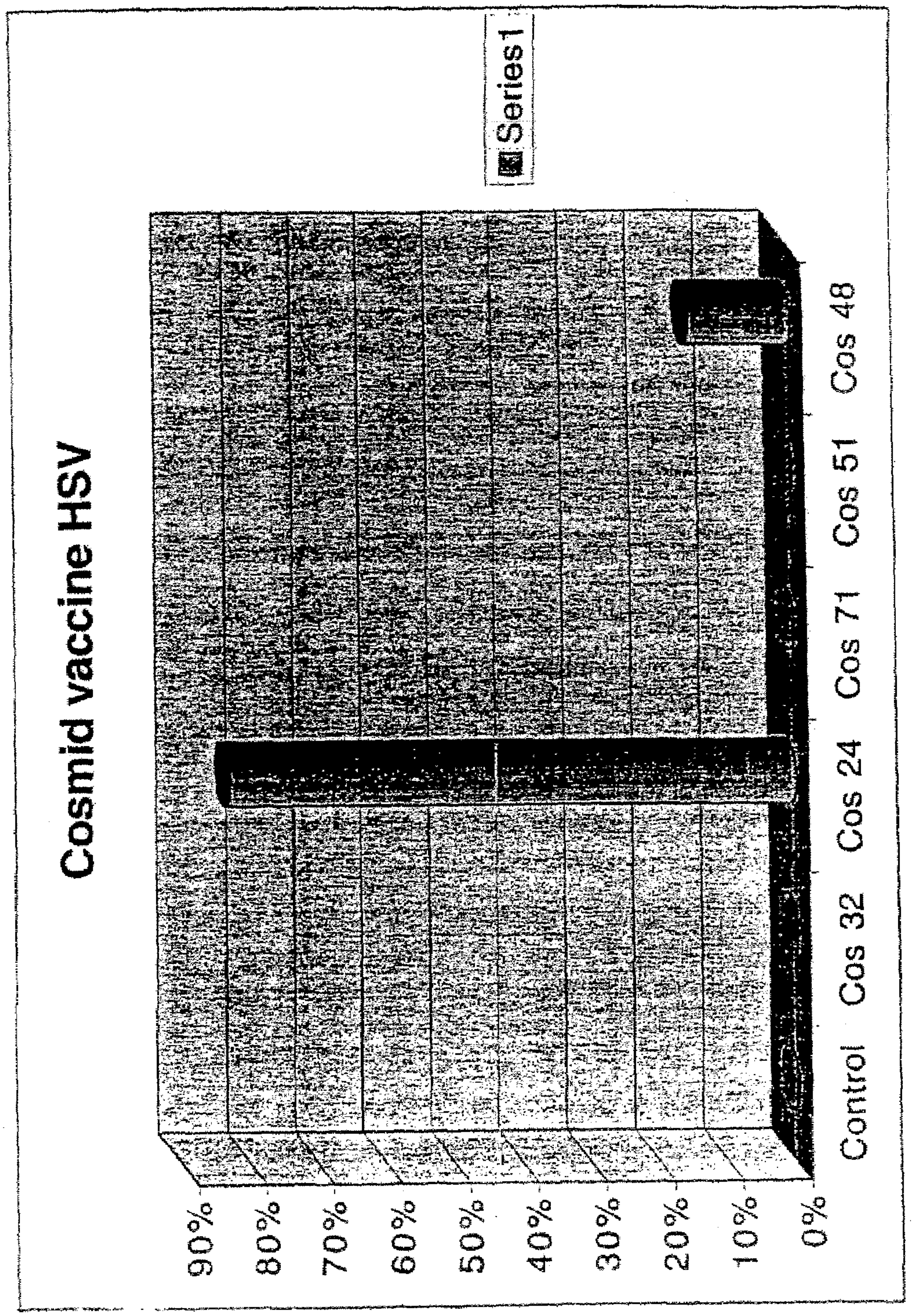
FIG. 3 shows data showing the levels of protection against HSV-1 infection achieved following prophylactic administration of cosmids described in FIGS. 1 and 2.

The present invention provides cosmids and their use as vectors to deliver genetic material to an individual. According to some aspects of the present invention, cosmids are provided and administered to individuals in order to deliver DNA that encodes an immunogenic protein or proteins to an individual in order to effect the induction of an immune response against such immunogens. According to some aspects of the present invention, cosmids are provided and administered to individuals in order to deliver DNA that encodes a protein or proteins which the individual requires but which is absent or present in insufficient quantities as a functional protein. According to some aspects of the present invention, cosmids are provided and administered to individuals in order to deliver DNA that encodes a non-immunogenic protein or proteins which will confer a therapeutic benefit to the individual.

The present invention provides improved methods of introduction of genetic material over DNA transfer technology which relies upon plasmids as the vector for gene delivery. According to the present invention, cosmids are provided instead of plasmids. Cosmids have several advantages over plasmids including the size of DNA constructs that can be made using cosmids. Cosmids are generally 50-100 kilobases of DNA and can be used to deliver much larger DNA constructs as compared to plasmids. Larger DNA constructs can be used to provide multiple coding sequences including multiple copies of the same coding sequence and/or multiple coding sequences. A single cosmid can be used to deliver genetic material capable of inducing immune responses against multiple pathogens for example. Furthermore, the ease of handling and inexpensive nature of DNA allow for an efficient means of screening for protective antigens. Genes can be sorted and systematically tested much more easily than proteins. The pathogenic agents and organism for which the vaccine is being produced to protect against is selected and an immunogenic protein is identified. The present invention provides the advantage of being able to include large portions of DNA on a single vector construct. In some embodiments, large portions of a pathogen genome may be included in a cosmid DNA construct. Such large coding regions provide the means to induce immune responses against multiple pathogen antigens. The identification of protective antigens can be facilitated by testing portions of genome to identify gene constructs which contain multiple coding sequences including one that encodes a protective antigen. Subcloning can then be used to identify the specific antigen involved in inducing the protective response.

In some embodiments, cosmids of the invention comprise coding sequences for multiple proteins. Such constructs can represent a single active agent capable of delivering immunogenic targets and conferring immunity against multiple pathogen antigens from more than one pathogen. The recent invention allows for the use of a single vector which can be used to deliver multiple immunogens, thus reducing the number of active agents to be produced and the number of vaccines to be administered.

In some embodiments, cosmids of the invention comprise coding sequences for multiple proteins. Such constructs can represent a single active agent capable of delivering one or more immunogenic targets as wells as one or more proteins which are useful to enhance or otherwise modulate the immune response generated against the immunogenic protein or proteins.

In some embodiments, cosmids of the invention comprise incomplete pathogen genomes which allow for the introduction of multiple pathogen antigens as a vaccines in a single construct. Thus, large portions of a pathogen's coding sequences can be introduced to provide multiple targets while insuring that no infectious organism or virus can be produced. In pathogens with large genomes, this technology is particularly useful because it allows for the administration of a vaccine that includes multiple targets in cases where it is not known which antigen can be the target for a protective or therapeutic immune response.

In some embodiments, cosmids of the invention comprise nucleotide sequences that encode non-immunogenic proteins which confer a therapeutic benefit when administered. Such non-immunogenic proteins may replace non-functioning or partially functioning genes, mutant genes and the like. In such embodiments, the cosmids are used in replacement gene therapy. In some embodiments, the non-immunogenic proteins are proteins which are delivered to induce a specific effect that will provide a therapeutic benefit to the patient. In such embodiments, the cosmids are used in gene therapy as an alternative to administration of therapeutic proteins.

In preferred embodiments, the individual is a mammal, fish or avian species. In some preferred embodiments, the individual is a human, bovine, ovine, porcine, equine, canine and feline species.

In some embodiments, the cosmid that is at least 50 kilobases of DNA. In some embodiments, the cosmid that is at least 80 kilobases of DNA. In some embodiments, the cosmid that is at least 100 kilobases of DNA. In some embodiments, the cosmid used as a vector is the backbone of backbone of the HSV-1 constructs shown in FIG. 2 into which coding nucleotide sequences may be inserted. FIG. 2 shows constructs which contains fragments of the HSV-1 genome. In some embodiments, the cosmid is cosmid 24. FIG. 1 shows the various fragments of the HSV-1 genome inserted into the cosmids shown in FIG. 2. A cosmid-based system for constructing mutants of herpes simplex virus type 1. Cosmids are constructed as described in Cunningham, C. et al. Virology. 1993 November; 197(1):116-24, which is incorporated herein by reference.

In some embodiments, the constructs are inserted into yeast artificial chromosomes (YACs) which serve as vectors in place of cosmids. The disclosure herein as relating to cosmids is intended to further describe similar DNA constructs which employ YACs as the vector.

Cosmids include coding nucleotide sequences that encode one or more immunogens and/or one or more non-immunogenic proteins. In some embodiments, the cosmid includes coding nucleotide sequences that encode multiple proteins.

Coding nucleotide sequences are in expressible form. That is, the codons which encode the protein are compatible with and capable of being translated by the cells of the individual to whom or to which the cosmid is administered. Furthermore, the coding nucleotide sequences are operably linked to regulatory elements necessary for expression in the cells of the individual to whom or to which the cosmid is administered. In some preferred embodiments, the regulatory elements are those which are natively linked to the coding nucleotide sequences provided such elements are functional individual. For example, if the coding nucleotide sequences encodes a human protein and the individual is a human, the human promoter and polyadenylation sequences are linked the coding sequence and are used to express the coding sequence. Likewise, if the coding nucleotide sequences encodes a pathogen antigen that is expressed by the pathogen in a human and the individual is a human, the pathogen promoter and polyadenylation sequences are linked the coding sequence and are used to express the coding sequence. In some embodiments, heterologous regulatory sequences are linked to the coding nucleotide sequences.

The regulatory elements necessary for gene expression of a DNA molecule include: a promoter, an initiation codon, a stop codon, and a polyadenylation signal. In addition, enhancers are often required for gene expression. It is necessary that these elements be operable linked to the sequence that encodes the proteins and that the regulatory elements are operably in the individual to whom they are administered.

Initiation codons and stop codon are generally considered to be part of a coding nucleotide sequence that encodes the protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (such as the HIV Long Terminal Repeat (LTR) promoter, Moloney virus, ALV, Cytomegalovims (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to bovine growth hormone polyadenylation signal, SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

In some embodiments, the coding sequences are operably linked to their native regulatory sequences provided such regulatory sequences are operable in the individual to whom the cosmid is administered. In embodiments where incomplete pathogen genomes that include multiple coding sequences are inserted into cosmids, the advantage if using native regulatory sequences that are functional in the individual allow for a single insertion of multiple genes. In some embodiments, the incomplete pathogen genome is an incomplete viral genome. In some embodiments, the incomplete pathogen genome is an incomplete herpes virus simplex I genome.

In some preferred embodiments, the present invention provides methods of inducing an immune response in an individual against an immunogen. The methods comprise the step of administering to the individual a cosmid that is at least 50 kilobases of DNA. The cosmids used in this aspect of the invention can include coding nucleotide sequences that encode one or more proteins including at least one immunogen. In some embodiments, the cosmid includes coding nucleotide sequences that encode multiple immunogens. In some embodiments, the cosmid includes coding nucleotide sequences that encode one or more other proteins in addition to one or more immunogens. In each case, the coding nucleotide sequences are operably linked to regulatory elements that are functional in cells of the individual. This, when the cosmid is administered to tissue of the individual, it is taken up by cells in the individual where the coding nucleotide sequences are expressed. The immunogen is produced and an immune response against it is induced in the individual.

In some embodiments, the immunogen is a pathogen immunogen. In order to produce a genetic vaccine to protect against pathogen infection, genetic material which encodes immunogenic proteins against which a protective immune response can be mounted must be included in the genetic construct. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material which encodes many pathogen antigens. For example, several viral genes may be included in a single construct thereby providing multiple targets. In addition, multiple inoculants which can be delivered to different cells in an individual can be prepared to collectively include, in some cases, a complete or, more preferably, an incomplete such as a near complete set of genes in the vaccine. For example, a complete set of viral genes may be administered using two constructs which each contain a different half of the genome which are administered at different sites. Thus, an immune response may be invoked against each antigen without the risk of an infectious virus being assembled. This allows for the introduction of more than a single antigen target and can eliminate the requirement that protective antigens be identified.

Tables 1 and 2 include lists of some of the pathogenic agents and organisms for which genetic vaccines can be prepared to protect an individual from infection by them. In some preferred embodiments, the methods of immunizing an individual against a pathogen are directed against intracellular pathogens. In some preferred embodiments, the methods of immunizing an individual against malaria or tuberculosis. In some preferred embodiments, the methods of immunizing an individual against a virus. In some preferred embodiments, the methods of immunizing an individual against HIV, HSV, HTLV or HBV.

In some embodiments, a cosmid that comprises the coding sequence for a pathogen antigen is administered to an individual who is not infected by the pathogen and the immune response that is induced is a protective immune response. In some embodiments, a cosmid that comprises the coding sequence for a pathogen antigen is administered to an individual who is infected by the pathogen and the immune response that is induced is a therapeutic immune response.

Another aspect of the present invention provides a method of conferring a broad based protective immune response against hyperproliferating cells that are characteristic in hyperproliferative diseases and to a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. As used herein, the term "hyperproliferative-associated protein" is meant to refer to proteins that are associated with a hyperproliferative disease. To immunize against hyperproliferative diseases, a genetic construct that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins which are found at higher levels in tumor cells including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include Vβ-3, Vβ-14, Vβ-17 and Vα-17. Thus, vaccination with a DNA construct that encodes at least one of these proteins will elicit an immune response that will target T cells involved in RA. See: Howell, M. D., et al., 1991 *Proc. Natl. Acad. Sci. USA* 88:10921-10925; Paliard, X., et al., 1991 *Science* 253:325-329; Williams, W. V., et al., 1992 *J. Clin. Invest.* 90:326-333; each of which is incorporated herein by reference.

In MS, several specific variable regions of TCRs which are involved in the disease have been characterized. These TCRs include Vβ-7 and Vα-10. Thus, vaccination with a DNA construct that encodes at least one of these proteins will elicit an immune response that will target T cells involved in MS. See: Wucherpfennig, K. W., et al., 1990 *Science* 248:1016-1019; Oksenberg, J. R., et al., 1990 *Nature* 345:344-346; each of which is incorporated herein by reference.

In scleroderma, several specific variable regions of TCRs which are involved in the disease have been characterized. These TCRs include Vα-6, Vβ-8, Vβ-14 and Vα-16, Vα-3C, Vα-7, Vα-14, Vα-15, Vα-16, Vα-28 and Vα-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 *Sequence of Proteins of Immunological Interest* U.S. Department of Health and Human Services, Bethesda Md., which is incorporated herein by reference. In addition, a general method for cloning functional variable regions from antibodies can be found in Chaudhary, V. K., et al., 1990 *Proc. Natl. Acad. Sci. USA* 87:1066, which is incorporated herein by reference.

In some preferred embodiments related to immunization applications, the genetic construct contains nucleotide sequences that encode one or more target immunogens and further include genes for proteins which enhance the immune response against such target proteins. Examples of such genes are those which encode cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10 and IL-12. In some embodiments, it is preferred that the gene for GM-CSF is included in genetic constructs used in immunizing compositions.

In some of the embodiments of the invention that relate to gene therapy, the gene constructs contain either compensating genes or genes that encode therapeutic proteins. Examples of compensating genes include a gene which encodes dystrophin or a functional fragment, a gene to compensate for the defective gene in patients suffering from cystic fibrosis, an insulin, a gene to compensate for the defective gene in patients suffering from ADA, and a gene encoding Factor VIII. Examples of genes encoding therapeutic proteins include genes which encodes erythropoietin, interferon, LDL receptor, GM-CSF, IL-2, IL-4 and TNF. Additionally, genetic constructs which encode single chain antibody components which specifically bind to toxic substances can be administered.

According to some embodiments, methods of treating an individual susceptible to or suffering from a diseases associated with a genetic defect which results in the non-production or under production of a protein or the production of a non-functioning or partially functioning protein are provided. In such methods, cosmids that include DNA that encodes a protein to compensate for the non-produced, underproduced, non-functioning or partially functioning protein, is administered to an individual. The cosmid comprises at least 50 kilobases of DNA, preferable at least 80 kilobases of DNA, more preferably at least 100 kilobases of DNA, including a coding nucleotide sequence that encode said protein which compensates for the non-produced, underproduced, non-functioning or partially functioning protein. The coding nucleotide sequence is operably linked to regulatory elements that are functional in cells of said individual such that when the cosmid is taken up by cells in the individual, the coding nucleotide sequence is expressed and the protein which compensates for the non-produced, underproduced, non-functioning or partially functioning protein is produced in an amount effective to compensate for the non-produced, underproduced, non-functioning or partially functioning protein.

In some preferred embodiments, the dystrophin gene is provided as part of a mini-gene and used to treat individuals suffering from muscular dystrophy. In some preferred embodiments, a mini-gene which contains coding sequence for a partial dystrophin protein is provided. Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is chair-bound by age 13 and usually dies by age 20. In some patients, particularly those suffering from BMD, partial dystrophin protein produced by expression of a mini-gene delivered according to the present invention can provide improved muscle function.

In some preferred embodiments, genes encoding IL-2, IL-4, interferon or TNF are delivered to tumor cells which are either present or removed and then reintroduced into an individual. In some embodiments, a gene encoding gamma interferon is administered to an individual suffering from multiple sclerosis.

The present invention provides methods of delivering a protein to an individual comprising the step of administering to the individual a cosmid that comprises at least 50 kilobases of DNA including a coding nucleotide sequence that encode the protein. The coding nucleotide sequence is operably linked to regulatory elements that are functional in cells of the individual such that when the cosmid is taken up by cells in the individual, the coding nucleotide sequence is expressed and the protein is produced. In some embodiments, the protein is an immunogen and its expression leads to the induction of an immune response. In some embodiments, the protein is not immunogenic and its expression provides a therapeutic benefit to the individual.

In some embodiments, the cosmid is administered in combination with a DNA vaccine facilitator. Facilitating agents are also referred to as polynucleotide function enhancers or genetic vaccine facilitator agents. Facilitating agents are described in U.S. Pat. No. 5,593,972, U.S. Pat. No. 5,830,876, U.S. Pat. No. 5,817,637, U.S. Pat. No. 5,981,505, U.S. Pat. No. 5,739,118, U.S. Pat. No. 5,962,428, U.S. Pat. No. 5,837,533, and additionally include cationic lipids such as those described in U.S. Pat. No. 5,589,466. Facilitating agents which are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with or without a facilitating agent include growth factors, cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10, IL-12 and B7.2 as well as fibroblast growth factor, surface active agents such as immune-stimulating complexes (ISCOMS), Freund's incomplete adjuvant, LPS analog including monophosphoryl Lipid A (MPL), muramyl peptides, quinone analogs and vesicles such as squalene and squalene, and hyaluronic acid. In embodiments which relate to methods of immunizing, co-agents are selected which preferably enhance immune responses. In embodiments which relate to methods of immunosuppressing, co-agents are selected which do not enhance immune responses.

In some preferred embodiments, the genetic constructs of the invention are formulated with or administered in conjunction with a facilitator selected from the group consisting of benzoic acid esters, anilides, amidines, urethans and the hydrochloride salts thereof such as those of the family of local anesthetics.

The facilitators in some preferred embodiments may be a compound having one of the following formulae:

$$Ar—R^1—O—R^2—R^3$$

or $$Ar—N—R^1—R^2—R^3$$

or $$R^4—N—R^5—R^6$$

or $$R^4—O—R^1—R^7$$

wherein:

Ar is benzene, p-aminobenzene, m-aminobenzene, o-aminobenzene, substituted benzene, substituted p-aminobenzene, substituted m-aminobenzene, substituted o-aminobenzene, wherein the amino group in the aminobenzene compounds can be amino, $C_1$-$C_5$ alkylamine, $C_1$-$C_5$, $C_1$-$C_5$ dialkylamine and substitutions in substituted compounds are halogen, CL-CS alkyl and $C_1$-$C_5$ alkoxy;

$R^1$ is C═O;

$R^2$ is $C_1$-$C_{10}$ alkyl including branched alkyls;

$R^3$ is hydrogen, amine, $C_1$-$C_5$ alkylamine, $C_1$-$C_5$, $C_1$-$C_5$ dialkylamine;

$R^2$+$R^3$ can form a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle including a $C_1$-$C_{10}$ alkyl N-substituted heterocycle;

$R^4$ is Ar, $R^2$ or $C_1$-$C_5$ alkoxy, a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle and a $C_1$-$C_{10}$ alkoxy substituted heterocycle including a $C_1$-$C_{10}$ alkyl N-substituted heterocycle;

$R^5$ is C═NH;

$R^6$ is Ar, $R^2$ or $C_1$-$C_5$ alkoxy, a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle and a $C_1$-$C_{10}$ alkoxy substituted heterocycle including a $C_1$-$C_{10}$ alkyl N-substituted heterocycle; and.

$R^7$ is Ar, $R^2$ or $C_1$-$C_5$ alkoxy, a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle and a $C_1$-$C_{10}$ alkoxy substituted heterocycle including a $C_1$-$C_{10}$ alkyl N-substituted heterocycle.

Examples of esters include: benzoic acid esters such as piperocaine, meprylcaine and isobucaine; para-aminobenzoic acid esters such as procaine, tetracaine, butethamine, propoxycaine and chloroprocaine; meta-aminobenzoic acid esters including metabuthamine and primacaine; and paraethoxybenzoic acid esters such as parethoxycaine. Examples of anilides include lidocaine, etidocaine, mepivacaine, bupivacaine, pyrrocaine and prilocalne. Other examples of such compounds include dibucaine, benzocaine, dyclonine, pramoxine, proparacaine, butacaine, benoxinate, carbocaine, methyl bupivacaine, butasin picrate, phenacaine, diothan, luccaine, intracaine, nupercaine, metabutoxycaine, piridocaine, biphenamine and the botanically-derived bicyclics such as cocaine, cinnamoylcocaine, truxilline and cocaethylene and all such compounds complexed with hydrochloride.

In preferred embodiments, the facilitator is bupivacaine. The difference between bupivacaine and mepivacaine is that bupivacaine has a N-butyl group in place of an N-methyl group of mepivacaine. Compounds may have at that N, $C_1$-$C_{10}$. Compounds may be substituted by halogen such as procaine and chloroprocaine. The anilides are preferred.

The facilitating agent is administered prior to, simultaneously with or subsequent to the genetic construct. The facilitating agent and the genetic construct may be formulated in the same composition.

Bupivacaine-HCl is chemically designated as 2-piperidinecarboxamide, 1-butyl-N-(2,6-dimethylphenyl)-monohydrochloride, monohydrate and is widely available commercially for pharmaceutical uses from many sources including from Astra Pharmaceutical Products Inc. (Westboro, Mass.) and Sanofi Winthrop Pharmaceuticals (New York, N.Y.), Eastman Kodak (Rochester, N.Y.). Bupivacaine is commercially formulated with and without methylparaben and with or without epinephrine. Any such formulation may be used. It is commercially available for pharmaceutical use in concentration of 0.25%, 0.5% and 0.75% which may be used on the invention. Alternative concentrations, particularly those between 0.05%-1.0% which elicit desirable effects may be prepared if desired. According to the present invention, about 250 μg to about 10 mg of bupivacaine is administered. In some embodiments, about 250 μg to about 7.5 mg is administered. In some embodiments, about 0.05 mg to about 5.0 mg is administered. In some embodiments, about 0.5 mg to about 3.0 mg is administered. In some embodiments about 5 to 50 μg is administered. For example, in some embodiments about 50 μl to about 2 ml, preferably 50 μl to about 1500 μl and more preferably about 1 ml of 0.25-0.50% bupivacaine-HCl and 0.1% methylparaben in an isotonic pharmaceutical carrier is administered at the same site as the vaccine before, simultaneously with or after the vaccine is administered. Similarly, in some embodiments, about 50 μL to about 2 ml, preferably 50 μl to about 1500 μl and more preferably about 1 ml of 0.25-0.50% bupivacaine-HCl in an isotonic pharmaceutical carrier is administered at the same site as the vaccine before, simultaneously with or after the vaccine is administered. Bupivacaine and any other similarly acting compounds, particularly those of the related family of local anesthetics may be administered at concentrations which provide the desired facilitation of uptake of genetic constructs by cells.

In some embodiments of the invention, the individual is first subject to injection of the facilitator prior to administration of the genetic construct. That is, up to, for example, up to a about a week to ten days prior to administration of the genetic construct, the individual is first injected with the facilitator. In some embodiments, the individual is injected with facilitator about 1 to 5 days, in some embodiments 24 hours, before or after administration of the genetic construct. Alternatively, if used at all, the facilitator is administered simultaneously, minutes before or after administration of the genetic construct. Accordingly, the facilitator and the genetic construct may be combined to form a single pharmaceutical compositions.

In some embodiments, the genetic constructs are administered free of facilitating agents, that is in formulations free from facilitating agents using administration protocols in which the genetic constructions are not administered in conjunction with the administration of facilitating agents.

An aspect of the present invention relates to pharmaceutical compositions useful in the methods of the present invention. The pharmaceutical compositions comprise cosmids that comprise a nucleotide sequence that encodes one or more proteins operably linked to regulatory elements necessary for expression in the cells of the individual. The pharmaceutical compositions further comprise a pharmaceutically acceptable carrier or diluent. The term "pharmaceutical" is well known and widely understood by those skilled in the art. As used herein, the terms "pharmaceutical compositions" and "injectable pharmaceutical compositions" are meant to have their ordinary meaning as understood by those skilled in the art. Pharmaceutical compositions are required to meet specific standards regarding sterility, pyrogens, particulate matter as well as isotonicity and pH. For example, injections or injectable pharmaceuticals are sterile and pyrogen free.

Pharmaceutical compositions according to the present invention may comprise about 1 ng to about 10,000 μg of DNA. In some preferred embodiments, the pharmaceutical compositions contain about 2000 μg, 3000 μg, 4000 μg or 5000 μg of DNA. In some preferred embodiments, the pharmaceutical compositions contain about 1000 μg of DNA. In some preferred embodiments, the pharmaceutical compositions contain about 10 ng to about 800 μg of DNA. In some preferred embodiments, the pharmaceutical compositions contain about 0.1 to about 500 μg of DNA. In some preferred embodiments, the pharmaceutical compositions contain about 1 to about 350 μg of DNA. In some preferred embodiments, the pharmaceutical compositions contain about 25 to about 250 μg of DNA. In some preferred embodiments, the pharmaceutical compositions contain about 100 μg DNA.

The pharmaceutical compositions according to the present invention which comprise cosmids are formulated according to the mode of administration to be used. One having ordinary skill in the art can readily formulate a vaccine or non-immunogenic therapeutic that comprises a genetic construct. In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free. Pharmaceutical compositions according to the invention include delivery components in combination with nucleic acid molecules which further comprise a pharmaceutically acceptable carriers or vehicles, such as, for example, saline. Any medium may be used which allows for successful delivery of the nucleic acid.

The pharmaceutical compositions of the present invention may be administered by any means that enables the active agent to reach the agent's site of action in the body of a mammal. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Because peptides are subject to being digested when administered orally, oral formulations are formulated to enterically coat the active agent or otherwise protect it from degradation in the stomach (such as prenuetralization). Parenteral administration includes intravenous drip, subcutaneous, intraperitoneal or intramuscular injection, pulmonary administration, e.g., by inhalation or insufflation, or intrathecal or intraventricular administration. In preferred embodiments, parenteral administration, i.e., intravenous, subcutaneous, transdermal, intramuscular, is ordinarily used to optimize absorption. Intravenous administration may be accomplished with the aid of an infusion pump. The pharmaceutical compositions of the present invention may be formulated as an emulsion.

According to some embodiments of the present invention, the genetic construct is administered to an individual using a needleless injection device. According to some embodiments of the present invention, the genetic construct is simultaneously administered to an individual intradermally, subcutaneously and intramuscularly using a needleless injection device. Needleless injection devices are well known and widely available. One having ordinary skill in the art can, following the teachings herein, use needleless injection devices to deliver genetic material to cells of an individual. Needleless injection devices are well suited to deliver genetic material to all tissue. They are particularly useful to deliver genetic material to skin and muscle cells. In some embodiments, a needleless injection device may be used to propel a liquid that contains DNA molecules toward the surface of the individual's skin. The liquid is propelled at a sufficient velocity such that upon impact with the skin the liquid penetrates the surface of the skin, permeates the skin and muscle tissue therebeneath. Thus, the genetic material is simultaneously administered intradermally, subcutaneously and intramuscularly. In some embodiments, a needleless injection device may be used to deliver genetic material to tissue of other organs in order to introduce a nucleic acid molecule to cells of that organ.

One skilled in the art would readily comprehend the multitude of pharmaceutically acceptable media that may be used in the present invention. Suitable pharmaceutical carriers are described in *Remington's Pharmaceutical Sciences*, A. Osol, a standard reference text in this field, which is incorporated herein by reference. Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral, intravenous, intrathecal or intraventricular administration may include sterile aqueous solutions which may also contain buffers, diluents and other suitable additives and are preferably sterile and pyrogen free. Pharmaceutical compositions which are suitable for intravenous administration according to the invention are sterile and pyrogen free. For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution The pharmaceutical compositions according to the present invention may be administered as a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The methods of the present invention are useful in the fields of both human and veterinary medicine. The Examples set out below include representative examples of aspects of the present invention. The Examples are not meant to limit the scope of the invention but rather serve exemplary purposes. In addition, various aspects of the invention can be summarized by the following description. However, this description is not meant to limit the scope of the invention but rather to highlight various aspects of the invention. One having ordinary skill in the art can readily appreciate additional aspects and embodiments of the invention.

EXAMPLE

DNA molecules made up of incomplete HSV-1 genome as described in FIG. 12 were inserted into cosmids as described in FIG. 2 and used to determine whether vaccination with such constructs would protect against HSV-2 infection. BALB/c mice were immunized by intramuscular injection with 100 μg DNA in bupivacaine one or two times and challenged with HSV-2 intravaginally. FIG. 3 shows protection data indicating that cosmid 24 is particularly useful. The HSV-1 insert in cosmid 24 contains coding sequence for a protective antigen. Each of the coding sequences of the HSV-1 insert in cosmid 24 may be individually subcloned into a plasmid or other vector. The subclones are used in challenge experiments and the specific protective antigen is identified and used in a vaccine. A vaccine containing a single HSV-2 coding sequence from the HSV-1 insert in cosmid 24 is provided. The vaccine may be a DNA vaccine such as a plasmid. The vaccine is used in methods of preventing and treating HSV-1 and HSV-2 infection.

TABLE 1

| | |
|---|---|
| Picornavirus Family Genera: | Rhinoviruses: (Medical) responsible for ~50% cases of the common cold.<br>Etheroviruses: (Medical) includes polioviruaes, coxsackieviruses, echoviruses, and human enteroviruses such as hepatitis A virus.<br>Apthoviruses: (Veterinary) these are the foot and mouth disease viruses. |
| Target antigens: | VP1, VP2, VP3, VP4, VPG |
| Calcivirus Family Genera: | Norwalk Group of Viruses: (Medical) these viruses are an important causative agent of epidemic gastroenteritis. |
| Togavirus Family Genera: | Alphaviruses: (Medical and Veterinary) examples include Senilis viruses, RossRiver virus and Eastern & Western Equine encephalitis.<br>Reovirus: (Medical) Rubella virus. |
| Flariviridue Family | Examples include: (Medical) dengue, yellow fever, Japanese encephalitis, St. Louis encephalitis and tick borne encephalitis viruses. |
| Hepatitis C Virus: | (Medical) these viruses are not placed in a family yet but are believed to be either a togavirus or a flavivirus. Most similarity is with togavirus family. |

TABLE 1-continued

| | |
|---|---|
| Coronavirus Family: (Medical and Veterinary) | Infectious bronchitis virus (poultry)<br>Porcine transmissible gastroenteric virus (pig)<br>Porcine hemagglutinating encephalomyelitis virus (pig)<br>Feline infectious peritonitis virus (cats)<br>Feline enteric coronavirus (cat)<br>Canine coronavirus (dog)<br>The human respiratory coronaviruses cause ~40 cases of common cold. EX. 224E, OC43<br>Note - coronaviruses may cause non-A, B or C hepatitis |
| Target antigens: | E1 - also called M or matrix protein<br>E2 - also called S or Spike protein<br>E3 - also called HE or hemagglutin-elterose glycoprotein (not present in all coronaviruses)<br>N - nucleocapsid |
| Rhabdovirus Family | Vesiliovirus |
| Genera: | Lyssavirus: (medical and veterinary) rabies |
| Target antigen: | G protein<br>N protein |
| Filoviridue Family: (Medical) | Hemorrhagic fever viruses such as Marburg and Ebola virus |
| Paramyxovirus Family: | Paramyxovirus: (Medical and Veterinary) |
| Genera: | Mumps virus, New Castle disease virus (important pathogen in chickens)<br>Morbillivirus: (Medical and Veterinary) Measles, canine distemper<br>Pneuminvirus: (Medical and Veterinary) Respiratory syncytial virus |
| Orthomyxovirus Family (Medical) | The Influenza virus |
| Bungavirus Family | Bungavirus: (Medical) California encephalitis, LA Crosse |
| Genera: | Phlebovirus: (Medical) Rift Valley Fever<br>Hantavirus: Puremala is a hemahagin fever virus<br>Nairvirus (Veterinary) Nairobi sheep disease<br>Also many unassigned bungaviruses |
| Arenavirus Family (Medical) | LCM, Lassa fever virus |
| Reovirus Family | Reovirus: a possible human pathogen |
| Genera: | Rotavirus: acute gastroenteritis in children<br>Orbiviruses: (Medical and Veterinary) Colorado Tick fever, Lebombo (humans) equine encephalosis, blue tongue |
| Retrovirus Family | Oncorivirinal: (Veterinary) (Medical) |
| Sub-Family: | feline leukemia virus, HTLVI and HTLVII<br>Lentivirinal: (Medical and Veterinary) HIV, feline immunodeficiency virus, equine infections, anemia virus<br>Spumavirinal |
| Papovavirus Family | Polyomaviruses: (Medical) BKU and JCU |
| Sub-Family: | viruses |
| Sub-Family: | Papillomavirus: (Medical) many viral types associated with cancers or malignant progression of papilloma |
| Adenovirus (Medical) | EX AD7, ARC., O.B. - cause respiratory disease - some adenoviruses such as 275 cause enteritis |
| Parvovirus Family (Veterinary) | Feline parvovirus: causes feline enteritis<br>Feline panleucopeniavirus<br>Canine parvovirus<br>Porcine parvovirus |
| Herpesvirus Family | |
| Sub-Family: | alphaherpesviridue |
| Genera; | Simplexvirus (Medical)<br>HSVI, HSVII<br>Varicellovirus: (Medical - Veterinary) pseudorabies - varicella zoster |
| Sub-Family - | betaherpesviridue |
| Genera: | Cytomegalovirus (Medical)<br>HCMV |

TABLE 1-continued

| | |
|---|---|
| | Muromegalovirus |
| Sub-Family: | Gammaherpesviridue |
| Genera: | Lymphocryptovirus (Medical)<br>EBV - (Burkitts lympho)<br>Rhadinovirus |
| Poxvirus Family | |
| Sub-Family: | Chordopoxviridue (Medical - Veterinary) |
| Genera: | Variola (Smallpox)<br>Vaccinia (Cowpox)<br>Parapoxivirus - Veterinary<br>Auipoxvirus - Veterinary<br>Capripoxvirus<br>Leporipoxvirus<br>Suipoxvirus |
| Sub-Family: | Entemopoxviridue |
| Hepadnavirus Family | Hepatitis B virus |
| Unclassified | Hepatitis delta virus |

TABLE 2

| | |
|---|---|
| Bacterial pathogens | Pathogenic gram-positive cocci include: pneumococcal; staphylococcal; and streptococcal. Pathogenic gram-negative cocci include: meningococcal; and gonococcal. Pathogenic enteric gram-negative bacilli include: enterobacteriaceae; *pseudomonas*, acinetobacteria and *eikenella*; melioidosis; salmonella; shigellosis; hemophilus; chancroid; brucellosis; tularemia; *yersinia* (*pasteurella*); *streptobacillus* moniliformis and spirilum; *listeria monocytogenes*; *erysipelothrix rhusiopathiae*; diphtheria; cholera; anthrax; donovanosis (granuloma inguinale); and bartonellosis. Pathogenic anaerobic bacteria include; tetanus; botulism; other clostridia; tuberculosis; leprosy; and other mycobacteria. Pathogenic spirochetal diseases include: syphilis; treponematoses: yaws, pinta and endemic syphilis; and leptospirosis. Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include rickettsial and rickettsioses. Examples of mycoplasma and chlamydial infections include: mycoplasma pneumoniae; lymphogranuloma venereum; psittacosis; and perinatal chlamydial infections. |
| Pathogenic eukaryotes | Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections. |

The invention claimed is:

1. A method of inducing a humoral and cellular immune response in an individual against Herpes Simplex Virus-1 antigens encoded by nucleotides 5938-44597 of Herpes Simplex Virus-1 genome comprising the step of administering to said individual a cosmid that comprises nucleotides 5938-44597 of Herpes Simplex Virus-1 genome, wherein said cosmid is taken up by cells in said individual, said coding nucleotide sequences are expressed and a cellular immune response and a humoral immune response-against antigens encoded by the coding nucleotide sequences are induced in said individual.

2. The method of claim 1 wherein said cosmid is administered to said individual in combination with a DNA vaccine facilitator.

3. The method of claim 1 wherein said cosmid is administered to said individual in combination with bupivacaine.

4. The method of claim 1 wherein said cosmid further comprises coding nucleotide sequences that encode a non-immunogenic immunomodulating protein.

* * * * *

UNITED STATES PATENT AND TRADEMARK OFFICE

CERTIFICATE OF CORRECTION

PATENT NO. : 8,529,884 B2
APPLICATION NO. : 10/168694
DATED : September 10, 2013
INVENTOR(S) : Weiner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2601 days.

Signed and Sealed this
Thirty-first Day of March, 2015

Michelle K. Lee
*Director of the United States Patent and Trademark Office*